(12) United States Patent
Hamou

(10) Patent No.: US 7,789,880 B2
(45) Date of Patent: Sep. 7, 2010

(54) DEVICE FOR RESECTION AND/OR ABLATION OF ORGANIC TISSUE BY MEANS OF HIGH-FREQUENCY CURRENT

(76) Inventor: Jacques Hamou, 2, Chaussee de la Muetta, FR-75016 Paris (FR)

( * ) Notice: Subject to any disclaimer, the term of this patent is extended or adjusted under 35 U.S.C. 154(b) by 168 days.

(21) Appl. No.: 11/741,339

(22) Filed: Apr. 27, 2007

(65) Prior Publication Data

US 2008/0009855 A1 Jan. 10, 2008

Related U.S. Application Data

(63) Continuation of application No. PCT/EP2005/011579, filed on Oct. 28, 2005.

(30) Foreign Application Priority Data

Oct. 29, 2004 (FR) .................................. 04 11627

(51) Int. Cl.
    *A61B 18/14* (2006.01)
(52) U.S. Cl. .............................. 606/45; 606/39; 606/40; 606/41; 606/49; 606/46; 607/116
(58) Field of Classification Search .................. 606/39, 606/45–48
    See application file for complete search history.

(56) References Cited

U.S. PATENT DOCUMENTS 3,601,126 A * 8/1971 Estes ........................... 606/35
3,805,791 A * 4/1974 Seuberth et al. ............... 606/47
3,955,578 A * 5/1976 Chamness et al. ............. 606/47
4,256,113 A * 3/1981 Chamness ..................... 606/47
5,437,665 A * 8/1995 Munro ......................... 606/47
5,910,150 A * 6/1999 Saadat ......................... 606/159
2002/0095152 A1* 7/2002 Ciarrocca et al. ............. 606/48

FOREIGN PATENT DOCUMENTS

| DE | 33 13 325 A1 | 10/1984 |
| EP | 0 448 857 A1 | 10/1991 |
| FR | 2 645 008 | 10/1990 |
| GB | 618528 | 2/1949 |
| WO | WO 95/30377 | 5/1994 |
| WO | WO 98/24372 | 11/1997 |

OTHER PUBLICATIONS

International Search Report, Jan. 31, 2006, 3 Pages.
International Preliminary Report on Patentability, May 1, 2007, 9 pages.

* cited by examiner

*Primary Examiner*—Michael Peffley
*Assistant Examiner*—Ronald Hupczey, Jr.
(74) *Attorney, Agent, or Firm*—St. Onge Steward Johnston & Reens LLC

(57) ABSTRACT

A device for resection and/or ablation of organic tissue by means of high-frequency current comprises, at the distal end, a loop that can be acted upon by high-frequency voltage and, in the proximal direction from the loop, at least one helix that can likewise be acted upon by high-frequency voltage, the arrangement of loop and helix being able to be moved in rotation about the longitudinal axis of the helix.

31 Claims, 4 Drawing Sheets

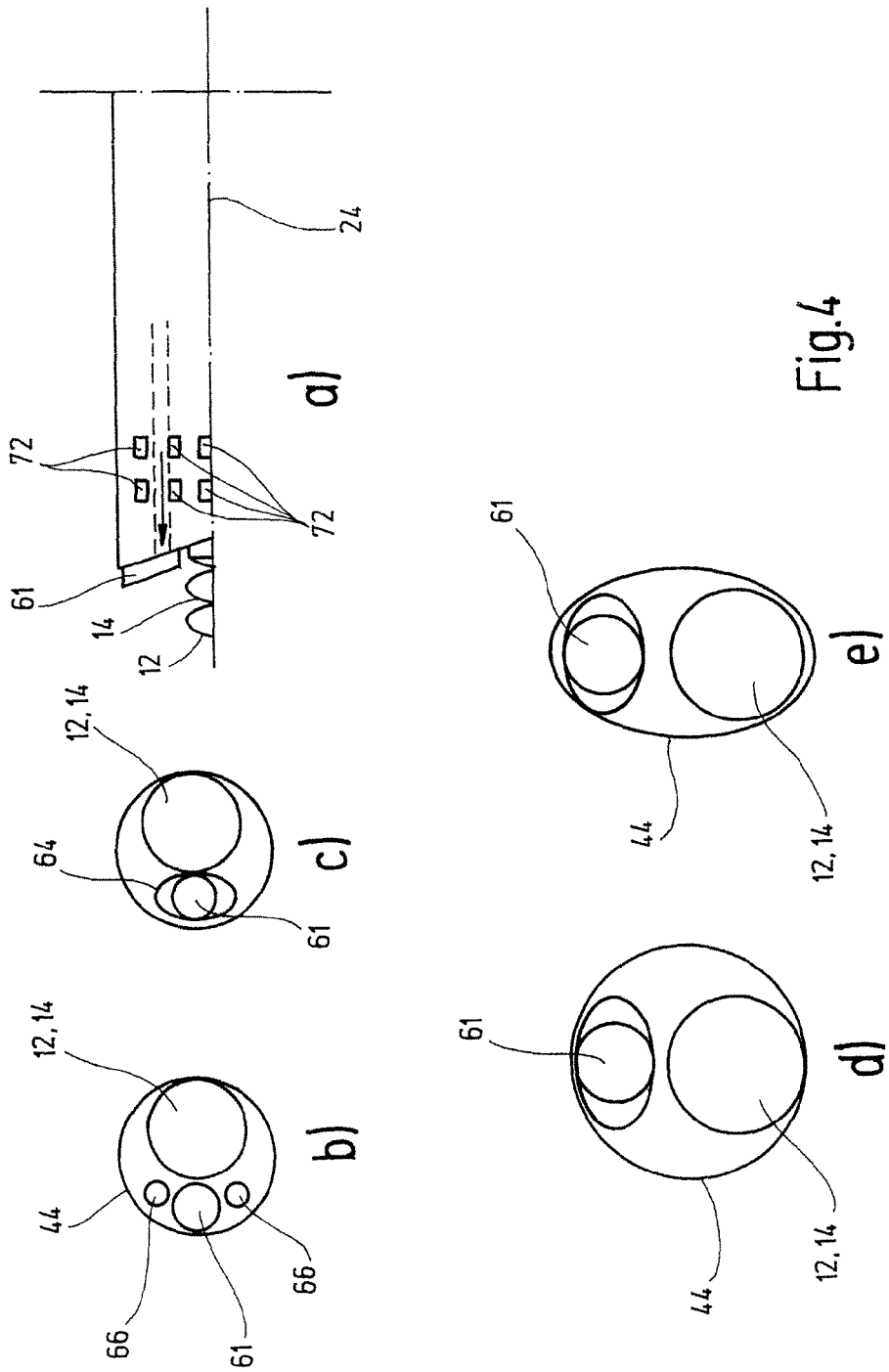

DEVICE FOR RESECTION AND/OR ABLATION OF ORGANIC TISSUE BY MEANS OF HIGH-FREQUENCY CURRENT

CROSS REFERENCE TO RELATED APPLICATIONS

The present application is a continuation of pending international patent application PCT/EP2005/011579 filed on Oct. 28, 2005 which designates the United States, and which claims priority of French patent application no. 0411627 filed on Oct. 29, 2004.

BACKGROUND OF THE INVENTION

The invention relates to a device for resection and/or ablation of organic tissue by means of high-frequency current, comprising, at a distal end, a loop that can be acted upon by high-frequency voltage.

Resection or ablation of organic structures is carried out, for example in hysteroscopy, to remove fibromas, polyps and tissue of the endometrium, and, in urology, to remove prostatic adenomas. Such resection or ablation of organic structures is conventionally performed using a resection instrument which, at the distal end, has an electrically conductive metal loop that can be acted upon by high-frequency current. To carry out a cutting procedure, the loop is subjected to monopolar or bipolar high-frequency voltage and, in order to make a cut intended to detach tissue, it is moved manually by the operating surgeon in the direction of the longitudinal axis of the resection instrument, specifically in a reciprocating movement, or only in one direction. The loop subjected to high-frequency current behaves in the manner of an electric scalpel. The loop in this way permits the detachment of tissue fragments of the same diameter. The bleeding associated with detachment of tissue can also be stanched using the same loop, after the tissue fragment has been released from the loop. The released tissue fragments must then be removed mechanically from the treatment area at another time.

A disadvantage of conventional devices of this kind for tissue resection by means of high-frequency current is that the duration of the intervention performed on the patient is protracted by the fact that the detached tissue fragments have to be removed from the treatment area by means of a further instrument, for example forceps. The duration of the intervention is protracted because it is necessary several times to change between the resection instrument for the process of detaching tissue and the removal instrument for the process of removing the detached tissue. A further disadvantage of the conventional devices is that their application is limited to the specific indication for which they are intended. Moreover, visual inspection is difficult with these devices.

SUMMARY OF THE INVENTION

The object of the invention is to develop a device of the type mentioned at the outset in such a way that the disadvantages described above are avoided, and, in particular, in such a way that the duration of a resection procedure can be reduced.

According to an aspect of the invention, a device for resecting organic tissue by means of a high-frequency current is provided, comprising at least one helix having a distal end and a longitudinal axis, a loop arranged at the distal end of the helix, the at least one helix and the loop being able to be moved in rotation about the longitudinal axis of the helix, and the at least one helix and the loop being able to be acted upon by high-frequency voltage.

With the rotating distal loop, tissue structures can advantageously be detached that are located in a frontal position with respect to the loop. With the at least one helix directly or indirectly adjoining the loop, it is possible, by contrast, to detach tissue structures that are located in a lateral position with respect to the at least one helix. By subjecting the loop and the at least one helix to high-frequency current, the detachment of tissue is improved still further under the effect of the high-frequency current. However, the bleeding that occurs during detachment of tissue can also be stanched by coagulation obtained by means of high-frequency current. A further effect of the rotating helix advantageously lies in the fact that detached tissue can now be entrained into the interior of the helix, and this detached tissue passing into the interior of the helix can be transported in the direction of the proximal end of the device by the rotation of the at least one helix. With the device according to the invention, it is therefore possible, without changing instruments, to perform uninterrupted resection of organic tissue while at the same time removing the detached tissue and stanching any bleeding. Compared to conventional devices, the device according to the invention thus makes it possible to reduce the duration of an intervention. The device is suitable for monopolar configurations, but also for bipolar ones.

In a preferred embodiment, the helix is designed as a double helix or multiple helix.

"Double helix" or "multiple helix" means here that the helix is composed of two or more helical and preferably cylindrical structures. The design of the at least one helix as a double helix or multiple helix leads to a greater stiffness of the windings of the helix during the resection of firmer tissue, particularly if the helix is elongate in the longitudinal direction, and, in addition, the entraining of detached tissue toward the proximal end can be further improved in this way.

As has been mentioned, the at least one helix is preferably designed such that it permits ablation of tissue located laterally with respect to the helix.

Moreover, the helix is preferably designed such that it permits transport of detached tissue in the proximal direction.

In another preferred embodiment, the helix is partially surrounded by a tube and is fixedly connected to the latter at least partially, and a distal portion of the helix protrudes from the tube by way of a distal opening of the tube.

The advantage of this is that the tube guarantees still greater stiffness of the windings of the helix. The distal portion of the helix protruding from the distal opening of the tube is then the active cutting portion, and at least the portion that is acted upon by high-frequency current. The fixed connection between helix and tube can be obtained by adhesive bonding, for example.

It is preferable if the tube can be moved in rotation by means of a motor.

In this way, a structurally simple drive mechanism is obtained, because the motor only has to move the tube in rotation, and the fixed connection of the helix to the tube means that the helix is then also moved in rotation.

In an alternative to the embodiment according to which the helix is connected fixedly to the tube at least partially, it is alternatively preferable if the helix is not fixedly connected to the tube, but instead is freely rotatable relative to the tube.

In this case, the tube is preferably stationary, and the helix is moved in rotation by means of the motor. An advantage of the embodiment according to which only the helix and the loop rotate is that the loop and the helix, which are subjected to wear, can be individually exchanged, whereas the tube, which is not subject to wear, or is not subject to any appreciable wear, can continue to be used.

It is also preferable if the helix extends at least approximately along the full length of the tube.

This measure ensures that the detached tissue is entrained or transported by the helix to the proximal end of the tube for simple removal and collection of the detached tissue in a container.

In an alternative to the aforementioned embodiment, it may also be preferable if the helix extends only along a partial length of the tube.

This measure is advantageous in particular with the above-mentioned measure according to which only the helix can be moved in rotation, since it makes the helix easier to exchange.

To supply current to the helix, blades can then preferably be used (two blades in the case of a double helix) which extend through the tube from the proximal HF attachment to almost the proximal end of the helix and are there in contact with the helix. The blades can be connected to the HF attachment via sliding contacts, in particular slip rings, because the blades have to co-rotate with the helix. In the case where the helix is designed to be exchangeable, the blades can remain within the tube.

The easier exchangeability of the loop and of the helix, without exchangeability of the tube, also has the advantage that a replacement loop with replacement helix can quickly be inserted into the device for different applications, without the device having to be further dismantled for this purpose.

In another preferred embodiment, the portion of the helix extending within the tube is electrically insulated.

The advantage of this is that the detached tissue transported through the tube, in the interior of the helix, does not adhere to the helix on account of heating.

It is likewise preferable if the tube is electrically insulated.

Danger to the operating physician is avoided in this way.

By contrast, the portion of the helix protruding from the tube is preferably not electrically insulated.

In another preferred embodiment, the portion of the helix protruding from the tube is formed from a stiff wire or is designed as a cutting blade with inwardly directed cutting edge.

The design of the helix as a cutting blade, with an inwardly directed cutting edge in its portion protruding from the tube, is particularly suitable for ensuring further morcellation of the detached tissue and for promoting the transport of the detached tissue into the interior of the at least one helix.

In another preferred embodiment, the portion of the helix extending within the tube, preferably having a variable width, has an inwardly directed cutting edge.

The inwardly directed cutting edge has the advantage of further promoting the proximal movement of tissue fragments that are passing into or have passed into the tube.

In other preferred embodiments, the distal opening of the tube can have a blunt or sharp edge.

The tube preferably has a diameter in the range from approximately 3 to approximately 6.5 mm, although diameters outside of this range may also be considered depending on the particular application.

The loop at the distal end of the device preferably has a semicircular shape, and it preferably has a diameter of from 4 to 7 mm.

Moreover, the loop is preferably formed from a stiff, electrically conductive wire or is designed as a cutting blade, and, in the latter case, the cutting edge is directed inward.

It is also preferable if the plane of the loop is inclined relative to the longitudinal axis, preferably slightly inclined, in such a way that tissue detached by the loop is oriented toward the interior of the helix.

The advantage of this is that forwardly located tissue detached by the loop can more easily pass into the interior of the helix for the purpose of being transported in the proximal direction.

In another preferred embodiment, the speed of rotation of the at least one helix and of the loop can be adjusted, preferably in a stepless manner, in a range from 0 to 1000 revolutions per minute.

The advantage of this is that the speed of rotation, and thus the cutting action, can be adapted to the strength of the tissue that is to be resected.

Provision can also preferably be made for fixed speeds of rotation to be preset, for example 20 revolutions per minute, 300 and 800 revolutions per minute, which can then be rapidly set via, for example, a corresponding actuating button.

Alternatively, or in addition to this, it is also preferable to provide for precise regulation within two ranges, for example in a range from 0 to 20 revolutions per minute and in a range from 300 to 800 revolutions per minute.

To adjust or control the speed of rotation, an actuating button preferably arranged on a handle at the proximal end of the device is provided, or a foot pedal is provided.

The actuating button arranged on the handle is preferably positioned such that it can be actuated by the same hand with which the device is gripped in the hand.

In another preferred embodiment, the high-frequency current is supplied by a high-frequency current generator and is configured for cutting and coagulation, the high-frequency current preferably being able to be switched on via a foot pedal.

The device according to the invention is preferably designed to permit cutting under the effect of high-frequency current and also to permit coagulation under the effect of high-frequency current, for which purpose the parameters of the high-frequency current, such as amplitude, frequency and, if appropriate, amplitude modulation, have to be suitably configured and adjusted. The operating physician can himself determine the duration and onset of the high-frequency current by switching it on and off.

In another preferred embodiment, a proximal end of the interior of the helix is connected, preferably by way of a hose, to a collecting container, for example a bottle, for receiving tissue fragments.

The advantage of this is that the tissue fragments transported from the distal end to the proximal end via the at least one helix are immediately conveyed into a container, without a further maneuver being required for this purpose.

In another preferred embodiment, a preferably adjustable underpressure can be applied to the interior of the helix or tube, for example by means of a pump.

The advantage of this is that, if the entraining effect of the rotating helix for transporting the detached tissue from the distal end to the proximal end is not sufficient, or is not entirely sufficient, the applied underpressure at least supports the withdrawal of the detached tissue fragments and ensures a complete withdrawal of the detached tissue fragments from the body.

In another preferred embodiment, an outer shaft is provided in order that the arrangement of tube, helix and loop can be received in the outer shaft, in which case the loop and the portion of the helix protruding from the tube protrude from the outer shaft.

The advantage of this is that, after it has been placed in the outer shaft, the arrangement of tube, helix and loop can be more easily guided through a trocar or a natural access into the operating site, and that the device can be provided with additional functions, such as visual inspection, irrigation and the like.

It is further preferable if the outer shaft is additionally designed to receive an endoscope.

With the endoscope, the course of the resection at the operating site can advantageously be visually monitored. The endoscope preferably has a forward oblique viewing lens, for example a 30° lens. Instead of a classical endoscope with an image-transmitting system made up of lenses, it is also possible to use an endoscope with image transmission through fiber-optics, or to use a video endoscope with distal image sensor.

It is also preferable if the outer shaft comprises at least one line for delivering irrigation fluid to the operating site and/or at least one line for suctioning fluid away from the operating site.

Blood can be flushed out by irrigation, as a result of which it is possible to maintain good visual monitoring, for example through the aforementioned endoscope.

Irrigation fluid is preferably supplied at low pressure. The irrigation fluid can be suctioned off in the proximal direction through the remaining space inside the outer shaft, the distal area of the outer shaft being able to be provided with a large number of suction orifices through which fluid can be sucked into the outer shaft.

Further advantages and features will become clear from the following description and from the attached drawing.

It will be appreciated that the aforementioned features and the features still to be explained below can be used not only in the respectively cited combination, but also in other combinations or singly, without departing from the scope of the present invention.

BRIEF DESCRIPTION OF THE DRAWINGS

Illustrative embodiments of the invention are depicted in the drawing are described in more detail below with reference to this drawing, in which:

FIGS. 4a) to 4e) show further details of the device from FIGS. 2 and 3 in different embodiment variants, FIG. 4a) showing a partial side view, and FIGS. 4b) to e) showing front views of the device.

DETAILED DESCRIPTION OF PREFERRED EMBODIMENTS

Figure 1:
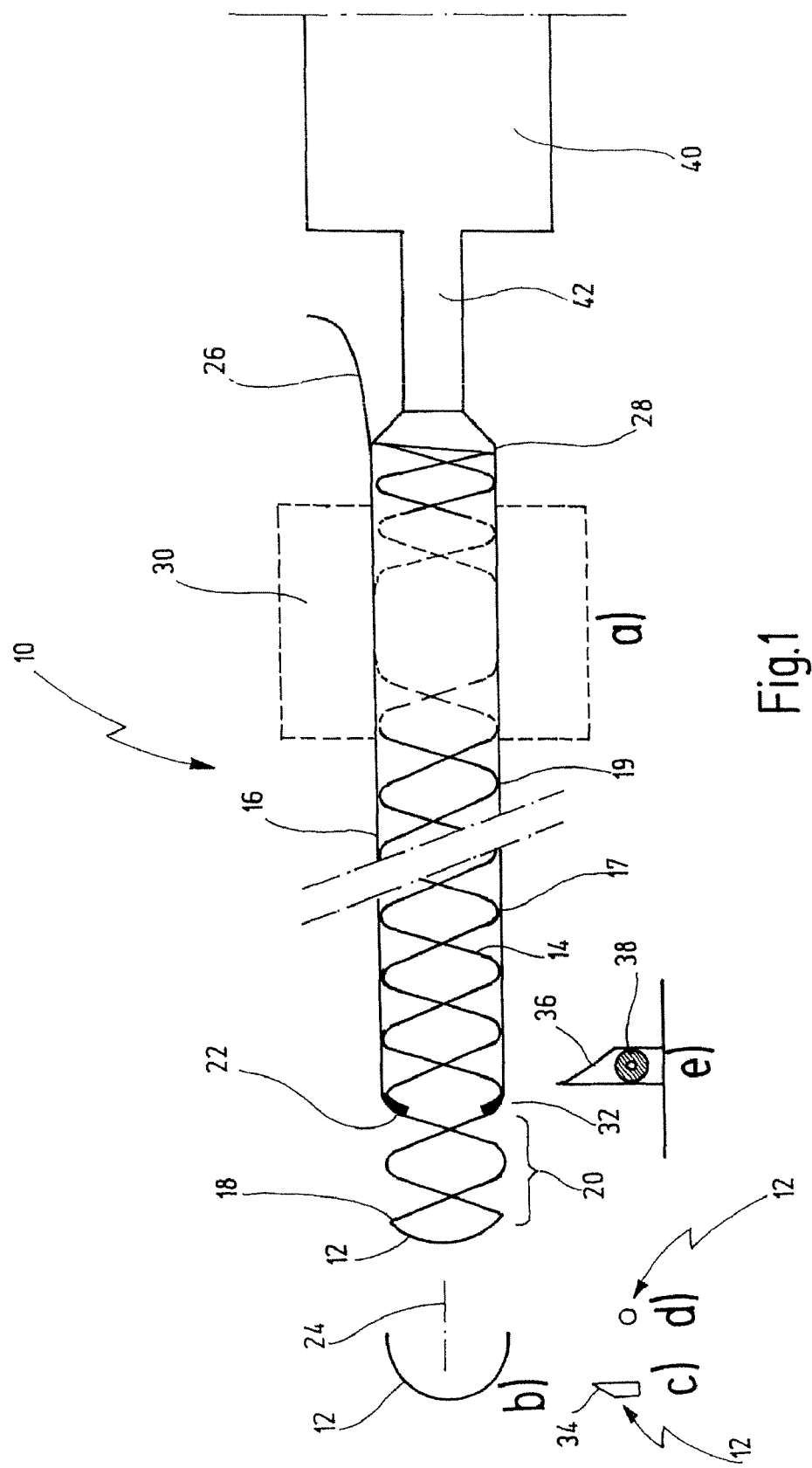
FIGS. 1a) to 1e) show a device for resection and/or ablation of organic tissue by means of high-frequency current, FIG. 1a) showing a schematic side view of the device, and FIGS. 1b) to 1e) showing isolated details of the device in some cases on an enlarged scale.

In FIG. 1a), a device for resection of organic tissue by means of high-frequency current is shown schematically and is designated overall by reference number 10.

The device 10 can be used, for example in hysteroscopy, to remove fibromas, polyps and endometrial tissue and, for example in urology, to remove prostatic adenomas.

At the outer distal end, the device 10 has a loop 12 that can be acted upon by high-frequency current. In the illustrative embodiment shown, the loop 12 is adjoined directly by a helix 14 which is designed as a double helix and which is arranged partially in a tube 16.

A distal end 18 of the helix 14 is connected to the distal loop 12. A distal portion 20 of the helix 14 protrudes from a distal opening 22 of the tube 16. The remaining portion of the helix 14, which extends into the tube 16, is fixedly connected to the tube 16 at least partially, for example by adhesive bonding.

Instead of an at least partially fixed connection of the helix 14 to the tube 16, an embodiment can also be considered in which the helix 14 is not connected to the tube 16, such that only the helix 14 can be moved in rotation, while the tube 16 is designed to be stationary.

At least the distal portion 20 of the helix 14 protruding from the tube 16 can also be acted upon by high-frequency current, specifically with the same high-frequency current with which the distal loop 12 can also be acted upon. The loop 12 and the distal portion 20 of the helix 14 are accordingly designed to conduct current. The portion of the helix 14 extending through the tube 16 can either be designed not to conduct current or have a corresponding insulation, such that the portion of the helix 14 extending into the tube 16 is electrically insulated from the distal portion 20.

In FIG. 1a), reference number 32 designates the electrical insulation by which the portion of the helix 14 extending into the tube 16 is insulated from the distal portion 20 of the helix 14.

According to FIG. 1b), the loop 12 has the shape of a semicircle, and the plane of the loop 12 is inclined relative to a longitudinal axis 24, i.e. forms an angle with the longitudinal axis 24, or, in other words, does not lie in the plane of the drawing in FIG. 1a).

The tube 16 is also electrically insulated. Instead of being made of metal, the tube 16 can also be made of a preferably hard plastic, into the inside wall of which the portion of the helix 14 extending into the tube 16 can also be worked.

The distal portion 20 and the loop 12 are contacted via an electrical supply line 26 extending through the tube 16, for example a wire provided with insulation, in which case the electrical supply line 26 is accordingly connected, or can be connected, to a high-frequency current generator (not shown).

In the case where only the helix 14 can be moved in rotation, and not the tube 16, the electrical supply line 26, which is then designed for example in the form of blades, i.e. elongate electrically conductive blades, is held on the device and is electrically contacted.

The helix 14 extends substantially along the full length of the tube 16, i.e. reaches as far as the proximal end 28 of the latter. However, the helix 14 can also terminate before the proximal end of the tube 16, for example by extending over a partial length of the tube 16 as far as a point 17 or 19 in FIG. 1a). This partial length can be 4 cm, for example. The portion 20 of the helix 14 that protrudes from the tube 16 can have a length of 4 to 6 mm, for example.

The helix 14 and the loop 12 can be moved in rotation together about the longitudinal axis 24 of the helix 14. For this purpose, a motor 30 is provided which, in the illustrative embodiment according to FIG. 1a), is arranged coaxially with respect to the longitudinal axis 24 and the tube 16 and moves the tube 16 itself in rotation. By means of the rotation of the tube 16, the helix 14 connected fixedly to it, and the loop 12 connected fixedly to the helix 14, are moved in rotation.

The motor 30 is an electric motor and can be designed as a hollow-shaft motor.

The loop 12 and the distal portion 20 of the helix 14 are not electrically insulated. When the tube 16, and with it the helix 14 and the loop 12, are moved in rotation, organic structures lying to the front, i.e. organic structures lying in the distal direction, can be cut by the loop 12 under the effect of high-frequency current, while lateral tissue structures can be cut with the distal portion 20 of the helix 14 under the effect of high-frequency current. Likewise, the loop 12 and the distal portion 20 of the helix 14 can be used for coagulation, in order to stanch the flow of blood.

The inclined position of the distal loop 12 means that, during the rotation of the loop 12, the tissue to be detached by the loop 12 is already oriented in such a way that it can pass into the interior of the helix 14 i.e. into the cylindrical inner space of the helix 14 and tube 16. To further strengthen this effect, the loop 12 can be designed as a cutting blade as seen in cross section according to FIG. 1c), in which case a cutting edge 34 is oriented toward the interior of the helix 14.

However, the loop 12 can also be formed from a stiff wire, for example steel wire, as is illustrated in FIG. 1d), which correspondingly has a round cross section for the loop 12. The diameter of the wire can be 0.25 mm for cutting, or 1 mm for coagulation, depending on the application. The choice of diameter will depend on whether cutting or coagulation is predominantly to be performed.

In the illustrative embodiment shown, the helix 14 is composed of two helical windings, which are offset by half the lead in the longitudinal direction, and is overall of cylindrical shape. In its distal portion extending within the tube 16, the helix 14 is used in particular to ensure that tissue that has been detached by means of the cutting blade 12 and the distal portion 20, and that has initially passed into the interior of the helix 14, is transported in the direction of the proximal end of the tube 16, such that the detached tissue can be withdrawn from the treatment area without additional manual intervention.

The distal portion 20 of the helix 14 that protrudes from the tube 16 can be formed from a stiff wire, in particular steel wire, or can be designed as a cutting blade with a cutting edge 36 facing the interior of the helix 14, as is shown in FIG. 1e). The design as a cutting blade with inwardly directed cutting edge 36 promotes the morcellation of the detached tissue and the entry of the detached tissue into the interior of the helix 14.

The portion of the helix 14 extending into the tube 16 can also have a cutting edge facing into the interior of the helix 14, to ensure that the resected or detached tissue fragments entering the tube 16 can be better conveyed in the direction of the proximal end 28 of the tube. As has already been mentioned, however, the portion of the helix 14 extending through the tube 16 is preferably electrically insulated, as is indicated in FIG. 1e) by reference number 38. Moreover, the portion of the helix 14 extending into the tube 16 can be of variable width or thickness.

The edge of the distal opening 22 of the tube 16 can itself be made sharp, and thus able to cut, or can be blunt.

The diameter of the tube 16 lies, for example, in a range from approximately 3 to approximately 6.5 mm, and the choice of the diameter of the tube 16, and thus also of the helix 14, may depend on the size of the organic structures that are to be resected. The length of the tube 16 is 10 to 30 cm, for example.

The speed of rotation of the motor 30, and thus also of the helix 14 and loop 12, can be adjusted within a range from 0 to approximately 1000 revolutions per minute, this adjustability preferably being stepless. The speed of rotation is adjusted according to the nature of the tissue that is to be detached. An actuating element for adjusting the speed of rotation will be described later with reference to the other figures.

Moreover, the speed of rotation of the motor 30 can also be set to fixed speeds of rotation, for example a speed of rotation of approximately 20 revolutions per minute and a speed of rotation of approximately 300 revolutions per minute, and another one at approximately 800 revolutions per minute.

The high-frequency current provided by the abovementioned high-frequency current generator, permitting the cutting of tissue and coagulation, is transmitted through the electrical supply line 26, which is electrically insulated, to the helix 14 and to the loop 12, the high-frequency current being configured accordingly for cutting and/or coagulation. In a manner not shown here, a foot pedal is provided for switching on the high-frequency current and for controlling the parameters of said high-frequency current. The device 10 is suitable for monopolar high-frequency current, but can also be designed, with suitable modification, for bipolar applications.

Moreover, the proximal end 28 of the tube 16 is connected, or is able to be connected, to a collecting container 40, for example a bottle, the connection being effected by way of a flexible hose 42, for example. Detached tissue transported in the proximal direction through the tube 16 is collected in the collecting container 40.

The withdrawal of detached tissue through the tube 16 can be further improved by the interior of the helix 14 or the interior of the tube 16 being subjected, for example by means of a pump, to an underpressure that reaches as far as the collecting container 40, in which case the underpressure or suctioning power can be adjusted to variable levels, for example within a range from 0 to −1 bar. An ENDOMAT® appliance, for example, can be used as the pump.

Further embodiments of the device 10 and their possible developments are now described with reference to FIGS. 2 to 4.

Figure 2:
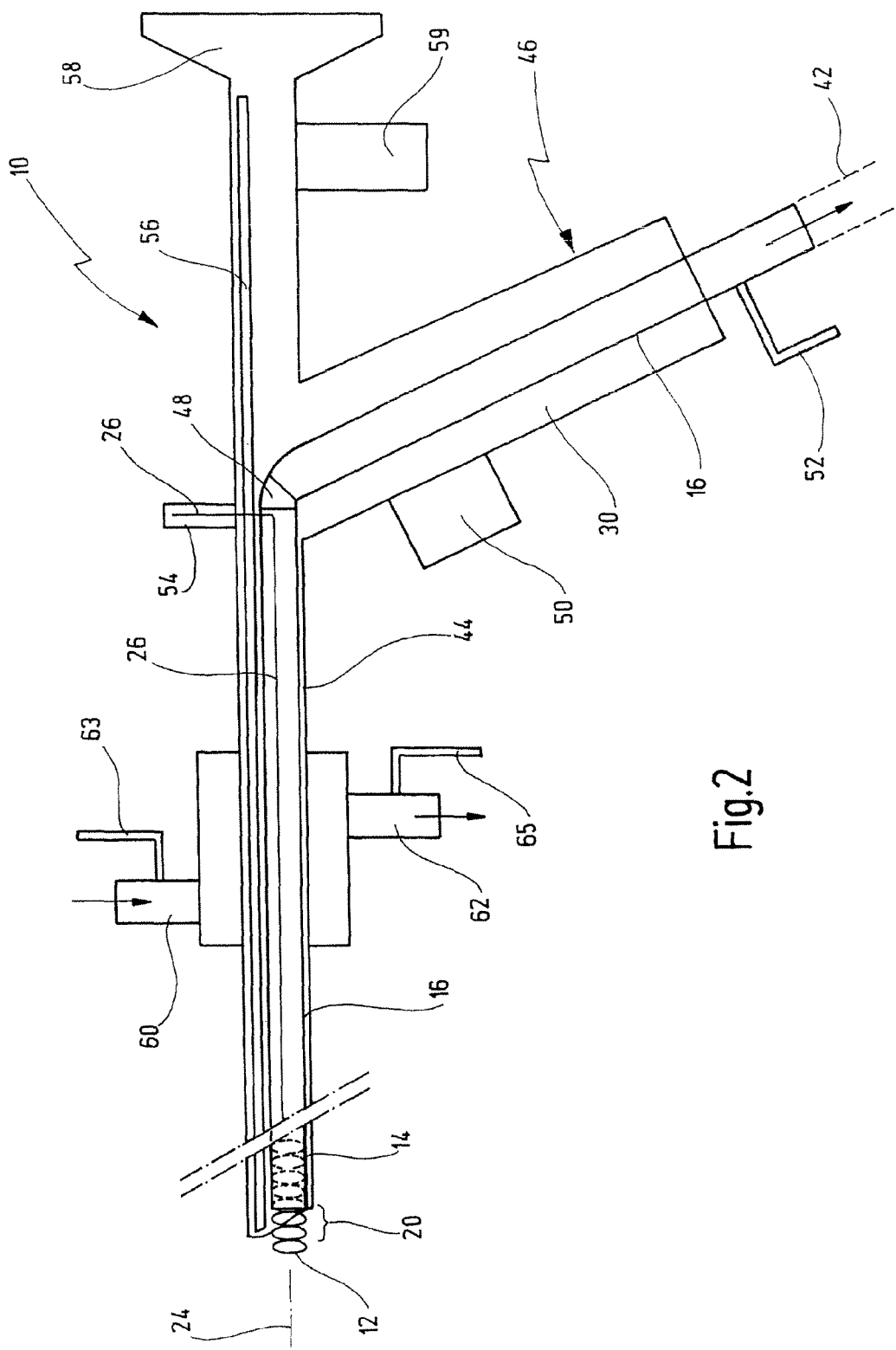
FIG. 2 shows a schematic side view of a device for resection and/or ablation of organic tissue by means of high-frequency current, in a modified design compared to FIG. 1.
Figure 3:
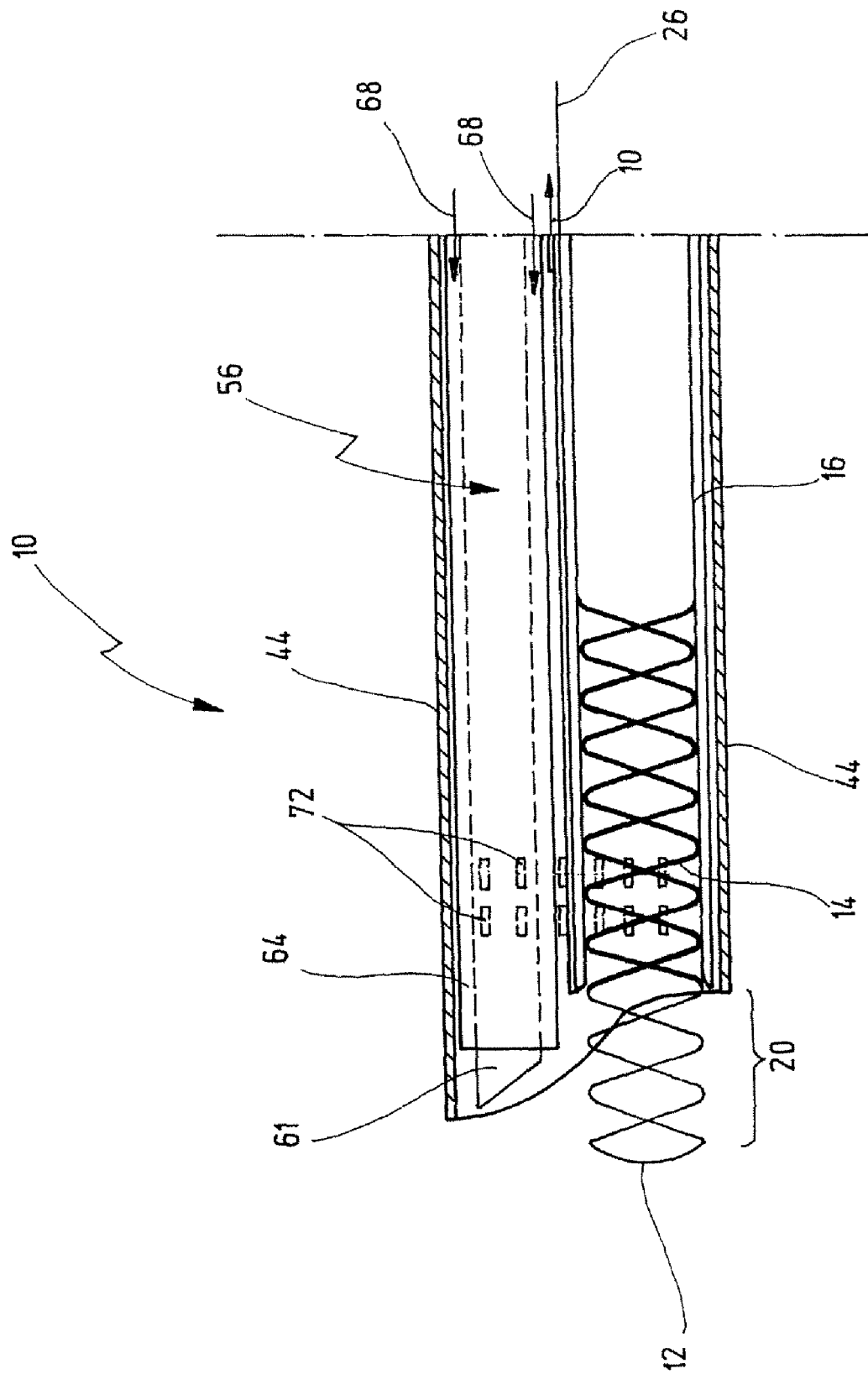
FIG. 3 shows a distal portion of the device from FIG. 2 in longitudinal section and on an enlarged scale.

In FIGS. 2 to 4, the same reference numbers as in FIG. 1 designate the same parts of the device 10, or parts that are the same in terms of their function.

According to FIGS. 2 to 4, the arrangement of tube 16, helix 14 and loop 12 is received in an outer shaft 44, in such a way that the tube 16, and with it the helix 14 and loop 12, can be moved in rotation in the outer shaft 44.

As will be seen from FIG. 3, the arrangement of tube 16, helix 14 and loop 12 is such that the distal portion 20, that is to say the portion of the helix 14 active for cutting, and the loop 14 protrude from the distal end of the outer shaft 44. In FIG. 3, the insulated portion of the helix 14 extending into the tube 16 is indicated by thicker lines.

In the device according to FIG. 1 and the device according to FIGS. 2 and 3, the tube 16, the helix 14 and the loop 12 can be designed as an exchangeable structural unit, particularly as a disposable part. In this case, different helix widths can be made available for the helix 14 that can be used with the outer shaft 44. In an embodiment as a disposable part, it is particularly recommended that the tube 16 be formed as a plastic part.

In the embodiment according to which only the helix 14 turns, and not the tube 16, the helix 14 can be exchanged together with the loop 12.

Helices 14 of different diameters and with different leads of the windings and different cross-sectional geometries of the helices 14 can be kept in stock.

On the outer shaft 44, a handle 46 is provided which is oriented obliquely with respect to the longitudinal axis 24 in the area of the proximal end of the device 10.

The outer shaft 44 can, for example, have an external diameter of 7 to 10 mm, but without being limited to this.

In the illustrative embodiment in FIG. 2, the tube 16 reaches into the handle 46, and the motor 30 is likewise received in the handle 46. In this embodiment, the tube 16 is accordingly provided with a joint 48 that transmits the rotation of the portion of the tube 16 in the handle 46 to the portion of the tube 16 extending parallel to the longitudinal axis 24. The joint 48 can be formed as a bevel gear or as a cardan joint, or as a flexible part of the tube 16 in this area, to name only some examples.

Instead of the arrangement in FIG. 1a), and instead of the arrangement in FIG. 2, the motor 30 can also be arranged outside the device 10. An external motor of this kind can then be connected to the device 10 via a shaft, in order to drive the tube 16.

The handle 46 also has a hand button, in particular a press-down switch 50, which can be actuated, for example, by the index finger of the hand that is gripping the handle 46, in order to steplessly adjust and control the speed of rotation of the tube 16 and thus of the helix 14 and loop 12. Moreover, the handle is provided with a cock, valve or the like 52 for adjusting the underpressure applied to the interior of the tube 16 in order to help transport detached tissue into the collecting container 40 (see FIG. 1). The cock, valve or the like 52 can also be positioned closer to the switch 50, such that it can be actuated ergonomically by the middle finger of the same hand that is gripping the handle 46.

The suction power through the tube 16 should be able to be finely controlled, such that the dependent size of the working area can be controlled. This is because too high a suction power can cause undesired collapse of the working area.

The outer shaft 44 is further provided with an attachment piece 54 for the HF cable with which the device 10 can be connected to the high-frequency current generator. Since the electrical supply line to the helix 14 has to co-rotate with the helix 14, the supply line is provided with a sliding contact, for example a slip ring, in order to ensure current transfer from the stationary attachment piece 54 to the helix 14.

The outer shaft 44 is also designed to receive an endoscope 56 which, in FIG. 2, is illustrated schematically at the proximal end with an eyepiece 58. Instead of the eyepiece 58, however, a video camera connected to the endoscope 56 can also be provided. Moreover, a light-guide attachment 59 is provided for connection of a light cable for illumination light.

Particularly in the arrangement according to FIG. 1a), in which the motor 30 is arranged coaxially with respect to the longitudinal axis 24 of the tube 16, instead of to the side of it as in FIG. 2, it is also possible to use an endoscope that has an image sensor at the distal end, such that there are no difficulties in moving the endoscope past the motor 30.

A distal end 61 of the endoscope 56 (see FIG. 3) is positioned approximately at the level of the distal portion 20 of the helix 14 or of the loop 12 and preferably has a forward oblique viewing lens, for example a 30° lens.

The endoscope 56 permits permanent visual monitoring of the cutting and coagulation procedure in the treatment area.

The diameter of the endoscope shaft and of the endoscope lens can be 3 mm, for example.

The outer shaft 44 also serves for supplying an irrigation fluid to the treatment site and for removing fluid from the treatment site. For this purpose, an irrigation attachment 60 with cock or valve or the like 63, and a suction attachment 62 with cock or valve or the like 65, are provided on the outer shaft 44, these two attachments being connected to a suitable suction and irrigation source (not shown).

The actuating elements 63 and 65 can also be positioned on the handle 46, such that they can be actuated, for example, by the thumb of the hand that is gripping the handle 46. The device 10 including the actuating elements 50 and 52 is then able to be operated using just one hand.

The permanent irrigation of the operating site and of the area of the distal portion 20 of the helix 14 and of the loop 12 is permitted by an uninterrupted flow of a nonconductive fluid, for example 1.5% strength GLYCOCOLLE, which is injected at low pressure into the operating site. The supply of irrigation fluid through the outer shaft 44 can take place, for example, through an inner tube 64 through which the endoscope 56 is also guided, and the remaining annular space between the endoscope 56 and the inner wall of the inner tube 64 then serves for the supply of irrigation fluid (see also FIGS. 4c), d) and e)).

Alternatively, thin hoses 66 can also lead from the irrigation attachment 60 to the distal end of the outer shaft 44.

The suctioning of fluids from the treatment site takes place via the suction attachment 62, the fluid being sucked through the remaining space in the interior of the outer shaft 44 between the tube 16 and the endoscope 56 or tube 64. In FIG. 3, the irrigation direction is indicated by arrows 68, and the suction direction is indicated by an arrow 70.

In a distal portion of the outer shaft 44, there are also openings or passages 72, for example along a length of 2 cm of the outer shaft 44, preferably about the entire circumference, through which fluid can be sucked into the outer shaft 44.

According to FIG. 4e), the outer shaft 44 can also have an oval cross section instead of a round one.

The device 10 permits detachment of frontal or lateral tissue structures and, similarly, the coagulation and removal of detached tissue from the operating site. No interruptions or instrument changes are needed to permit stanching of blood or removal of the detached tissue fragments. During the resection, a light traction can be exerted on that part of the tissue that is not to be resected, in order to better expose or even detach the base of this tissue structure, so as to avoid unwanted cutting of uninvolved structures.

In one application of the device 10, resection of a myoma, for example, can be initiated at a speed of rotation of the loop 12 and of the helix 14 of from 0 to 10 revolutions per minute, until the tissue is guided into the tube 16, specifically with the cock or valve 52 closed. During this phase, irrigation fluid is guided through the irrigation attachment 63 into the operating site and is led off via the suction attachment 62, the balance between supply of irrigation fluid and suctioning of the fluid being such that a slight underpressure is provided for distension in the operating area. As soon as detached tissue lies in the tube 16, the cock or valve 52 is then opened to suction the detached tissue from the tube 16 and is then closed again.

In the switched-off state, i.e. with the speed 0 or near 0, coagulation can be performed with the loop and with the distal portion 20 of the helix 14.

The faster speed of 50 to 300 revolutions per minute, with the cock or valve 52 partially opened, allows all fragile and soft tissue (for example of the endometrium) to be rapidly suctioned off. The rapid speed is mainly used for endometrial resections and for the resection of certain polyps.

The suctioning of the tissue is carried out preferably with the ENDOMAT® device. The switch 50 for regulating the speed of rotation of the helix 14 and of the loop 12 is designed to control the speed progressively and with great precision.

After distension of the operating site and insertion of the device 10, the tissue structure to be resected (myoma, polyp or prostate adenoma) is exposed. With the cock or valve 52 closed, the resection or ablation is initiated at low speed (between 0 and 10 revolutions per minute) and with high-frequency current switched on, as far as the obstruction at the distal end of the tube 16. At this point, the cock or valve 52 is opened and the combination of the positive pressure of the irrigation and the negative suction pressure via the cock or valve 52 and a rotation of the loop 12 and of the helix 14 at moderate speed permits a continuous resectioning of a myoma, for example, thus guaranteeing the three functions of resection, removal of detached tissue, and coagulation.

A further advantage of the helix 14 extending into the tube 16 is that as soon as tissue has been drawn into the tube 16, traction can be applied to the tissue, for example a myoma, because of the portion of the helix 14 extending into the tube 16, as a result of which it can be drawn to the cavum, as a result of which the intermediate part of the tissue not accessible in a conventional resection is drawn and consequently resected. In this way it is also possible to begin detaching the myoma or prostate adenoma from the wall, in order to gain a better view of the interface and be able to perform the resection much more safely.

What is claimed is:

1. A device for resecting organic tissue by means of a high-frequency current comprising:
   a first helix having a first distal end and a second helix having a second distal end, said first helix and said second helix having a common longitudinal axis, said first helix and said second helix each having helical windings wound round said common longitudinal axis,
   a loop having a first proximal end and a second proximal end, said first proximal end being connected to said first distal end of said first helix and said second proximal end being connected to said second distal end of said second helix,
   an outer shaft in which said first helix and said second helix are received, said loop and said first and second distal ends of said first and second helix protruding from said outer shaft,
   said first and second helix and said loop being able to be moved in rotation about said common longitudinal axis of said first and second helix relative to said outer shaft by means of a motor, and said first and second helix and said loop being able to be acted upon by high-frequency voltage.

2. The device of claim 1, wherein at least one of said first and second helix has a distal portion configured such that said at least one helix permits ablation of tissue located laterally with respect to said distal portion.

3. The device of claim 1, wherein said first and second helix permit transport of detached tissue in proximal direction.

4. The device of claim 1, wherein said first and second helix are partially surrounded by a tube, said first and second helix having a distal portion protruding from said tube through a distal opening of said tube.

5. The device of claim 4, wherein said first and second helix are fixedly connected to said tube.

6. The device of claim 5, wherein said tube is able to be moved in rotation.

7. The device of claim 4, wherein said first and second helix are freely rotatable relative to said tube.

8. The device of claim 4, wherein said tube has a length, and wherein said first and second helix extend at least approximately entirely along said length of said tube.

9. The device of claim 4, wherein said tube has a length, and wherein said first and second helix extend only partially along said length of said tube.

10. The device of claim 4, wherein a portion of said first and second helix which extends within said tube is electrically insulated.

11. The device of claim 4, wherein said tube is electrically insulated.

12. The device of claim 4, wherein said distal portion of said first and second helix protruding from said tube is not electrically insulated.

13. The device of claim 4, wherein said distal portion of said first and second helix protruding from said tube is formed from a stiff wire.

14. The device of claim 4, wherein said distal portion of said first and second helix protruding from said tube has a cutting blade with inwardly directed cutting edge.

15. The device of claim 4, wherein a portion of said first and second helix extending within said tube has an inwardly directed cutting edge.

16. The device of claim 4, wherein said opening of said tube has at least one of a blunt edge or a sharp edge.

17. The device of claim 4, wherein said tube has a diameter in a range from approximately 3 to approximately 6.5 mm.

18. The device of claim 1, wherein said loop has a semi-circular shape.

19. The device of claim 1, wherein said loop is formed from a stiff, electrically conductive wire.

20. The device of claim 1, wherein said loop has a cutting blade having a cutting edge directed inwardly.

21. The device of claim 1, wherein said loop defines a plane which is inclined relative to said longitudinal axis in such a way that tissue detached by said loop is oriented toward an interior of said first and second helix.

22. The device of claim 1, wherein a speed of rotation of said first and second helix and of said loop can be adjusted in a range from 0 to approximately 1000 revolutions per minute.

23. The device of claim 22, further comprising a proximal handle having an actuating button for adjusting said speed of rotation.

24. The device of claim 22, further comprising a foot pedal for adjusting said speed of rotation.

25. The device of claim 1, wherein said high-frequency voltage is supplied by a high-frequency voltage generator and is configured for at least one of cutting or coagulation.

26. The device of claim 25, further comprising a foot pedal for switching on said high-frequency voltage.

27. The device of claim 1, wherein a proximal end of an interior of said first and second helix is connected to a collecting container for receiving tissue fragments.

28. The device of claim 1, wherein an underpressure can be applied to an interior of said first and second helix.

29. The device of claim 1, wherein said outer shaft is additionally designed to receive an endoscope.

30. The device of claim 1, wherein said outer shaft comprises at least one line for delivering irrigation fluid to an operating site.

31. The device of claim 1, wherein said outer shaft comprises at least one line for suctioning fluid away from an operating site.

* * * * *

UNITED STATES PATENT AND TRADEMARK OFFICE
CERTIFICATE OF CORRECTION

| | | |
|---|---|---|
| PATENT NO. | : 7,789,880 B2 | Page 1 of 1 |
| APPLICATION NO. | : 11/741339 | |
| DATED | : September 7, 2010 | |
| INVENTOR(S) | : Jacques Hamou | |

It is certified that error appears in the above-identified patent and that said Letters Patent is hereby corrected as shown below:

On the Title page Item (76) should read,

Inventor: Jacques Hamou, 2, Chaussee de la Muette, FR-75016 Paris (FR)

Signed and Sealed this

Thirtieth Day of November, 2010

David J. Kappos
*Director of the United States Patent and Trademark Office*